United States Patent [19]

Nelson

[11] Patent Number: 4,878,504

[45] Date of Patent: Nov. 7, 1989

[54] ANKLE BRACE WITH COMPRESSION STRAPS

[76] Inventor: Ronald E. Nelson, 405 Sunset Ln., Cambridge, Minn. 55008

[21] Appl. No.: 223,083

[22] Filed: Jul. 22, 1988

[51] Int. Cl.⁴ .................................................. A61F 3/00
[52] U.S. Cl. ..................................... 128/80 H; 128/166
[58] Field of Search ............................. 128/80 H, 166

[56] References Cited

U.S. PATENT DOCUMENTS

| | | | |
|---|---|---|---|
| 332,727 | 12/1885 | McEwen . | |
| 1,374,669 | 4/1921 | McClellan | 128/166 |
| 1,717,609 | 6/1929 | Ludwig | 128/166 |
| 3,073,305 | 1/1963 | Biggs, Jr. et al. | 128/166 |
| 3,323,232 | 6/1967 | Danowsky | 36/2.5 |
| 3,327,410 | 6/1967 | Park Sr. et al. | 36/2.5 |
| 4,084,586 | 4/1978 | Hettick | 128/80 H |
| 4,237,874 | 12/1980 | Nelson | 128/80 H |
| 4,280,488 | 7/1981 | Polsky | 128/80 H |
| 4,313,433 | 2/1982 | Cramer | 128/80 H |
| 4,323,058 | 4/1982 | Petty | 128/166 |
| 4,527,556 | 7/1985 | Nelson | 128/80 H |
| 4,547,981 | 10/1985 | Thais | 128/80 H |
| 4,621,648 | 11/1986 | Ivany | 128/80 H |
| 4,640,025 | 2/1987 | DeRenzo | 128/166 |
| 4,651,726 | 3/1987 | Holland | 128/80 H |
| 4,724,847 | 2/1988 | Nelson | 128/80 H |
| 4,729,370 | 3/1988 | Kallassy | 128/80 H |

Primary Examiner—Edgar S. Burr
Assistant Examiner—Huong Q. Pham
Attorney, Agent, or Firm—Burd, Bartz & Gutenkauf

[57] ABSTRACT

An ankle brace having compression straps to give generalized support to the ankle region and specifically place it in a mild compressive state when relaxed such that upon engagement in rigorous activity, hyperextension of the ankle joint and undue twisting and turning as might lead to injury are avoided. The brace includes a base that wraps snuggly around the ankle and adjacent leg and foot regions. Lateral and medial compression straps are attached to lateral and medial sides of the base and wrap around the superior foot portion to bind it to the lower leg portion. End sections of the straps are fixed to the base along a relatively wide area of the sides of the base such that tension applied to the straps is distributed about a relatively large area on the side of the base. The end sections of the straps are fixed to the base by a plurality of spaced apart seams that extend along the sides of the base. These seams serve to distribute the tension force occasioned by tensioning the compression straps over a wider area of the base and foot.

17 Claims, 3 Drawing Sheets

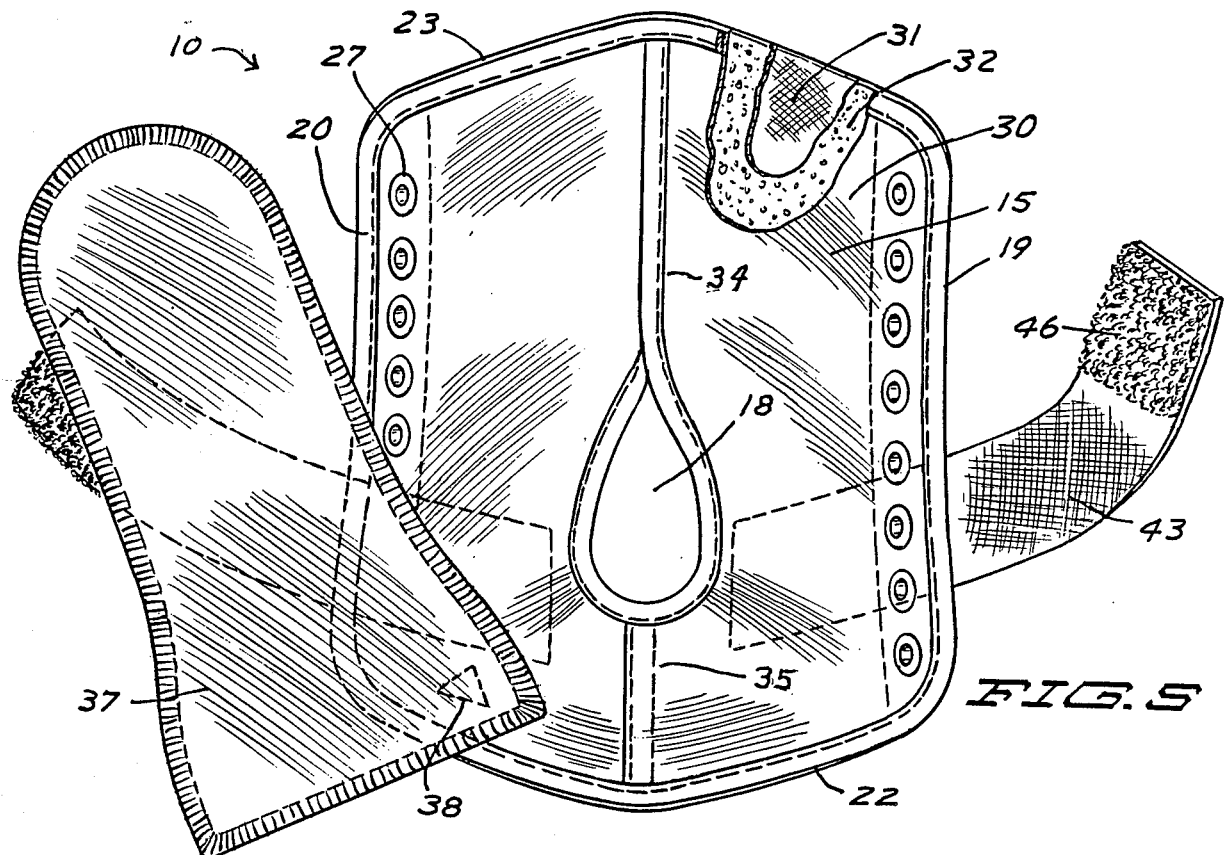
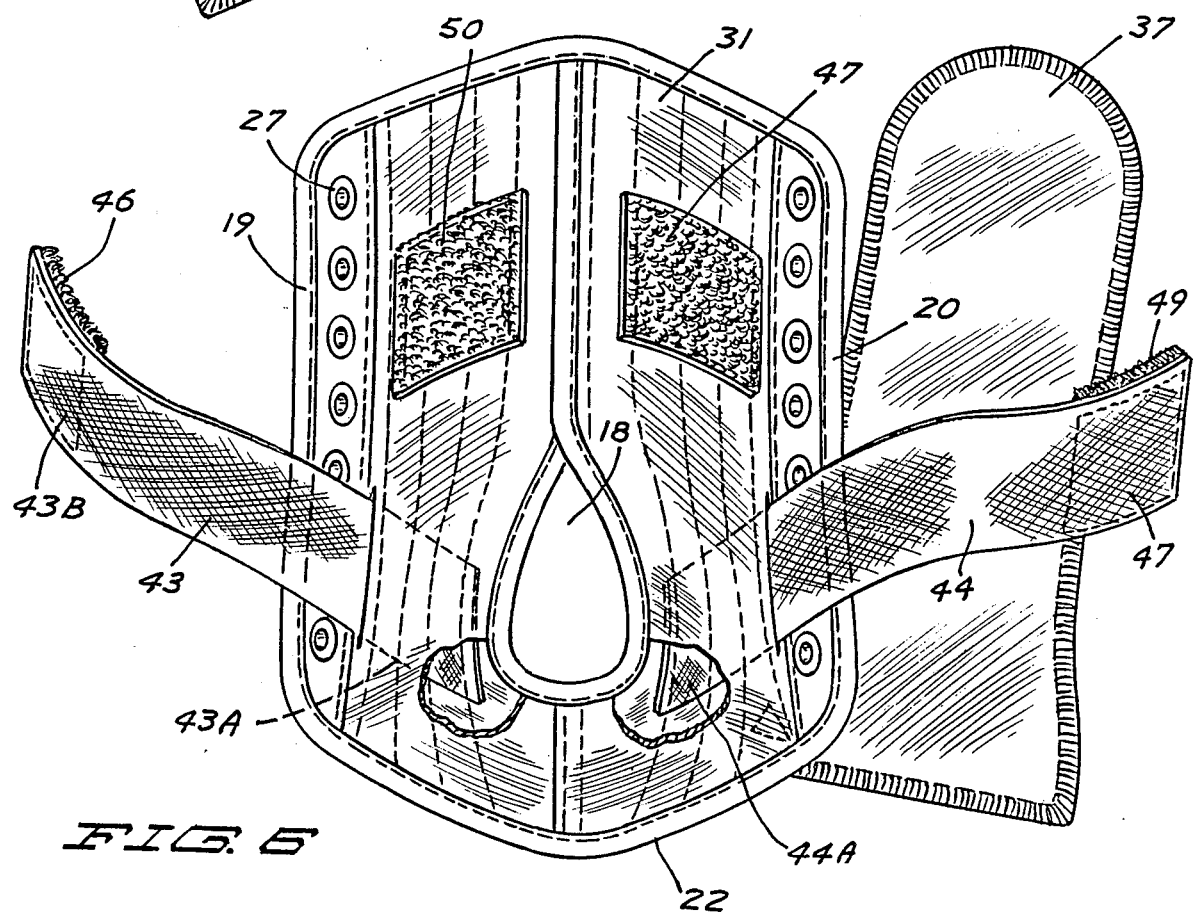

U.S. Patent Nov. 7, 1989 Sheet 3 of 3 4,878,504
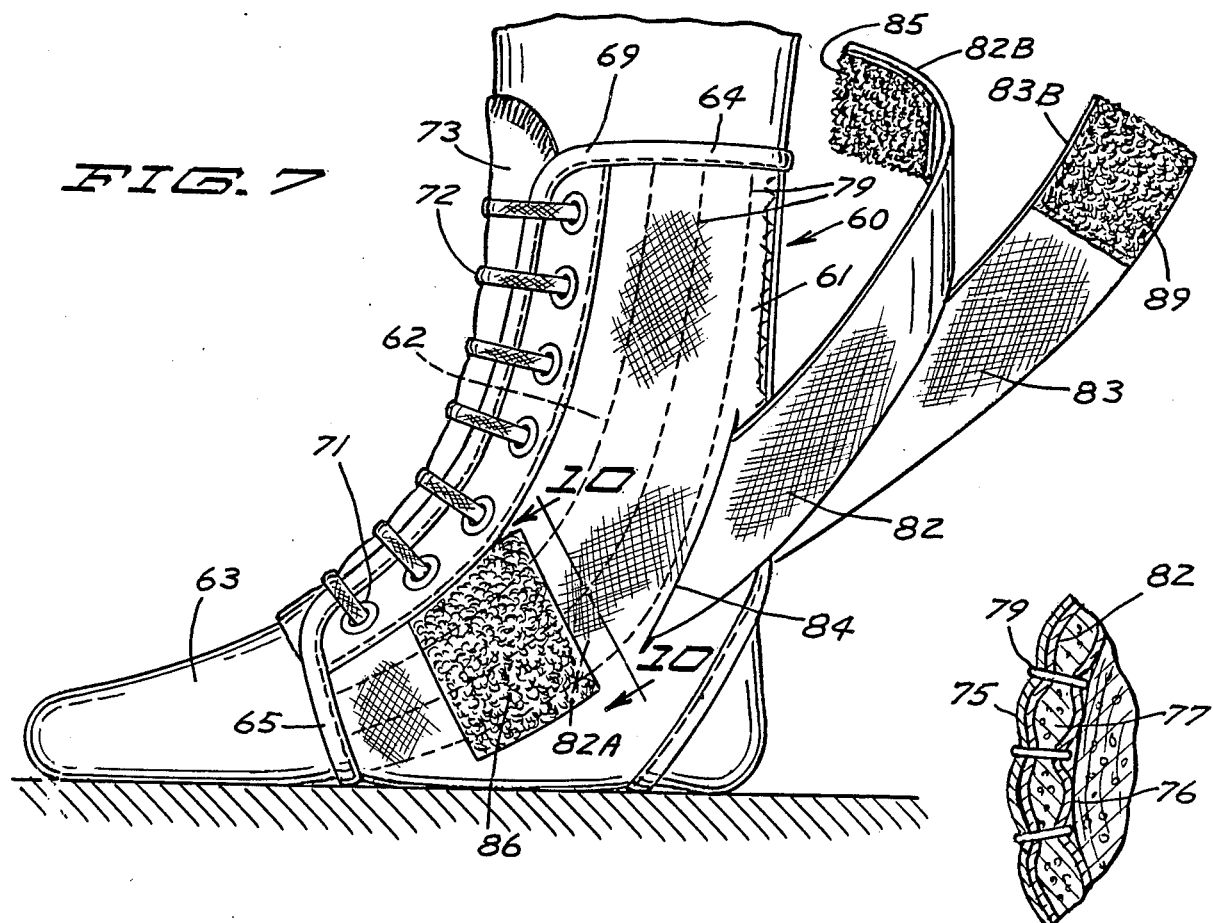
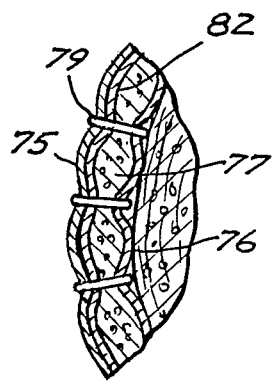
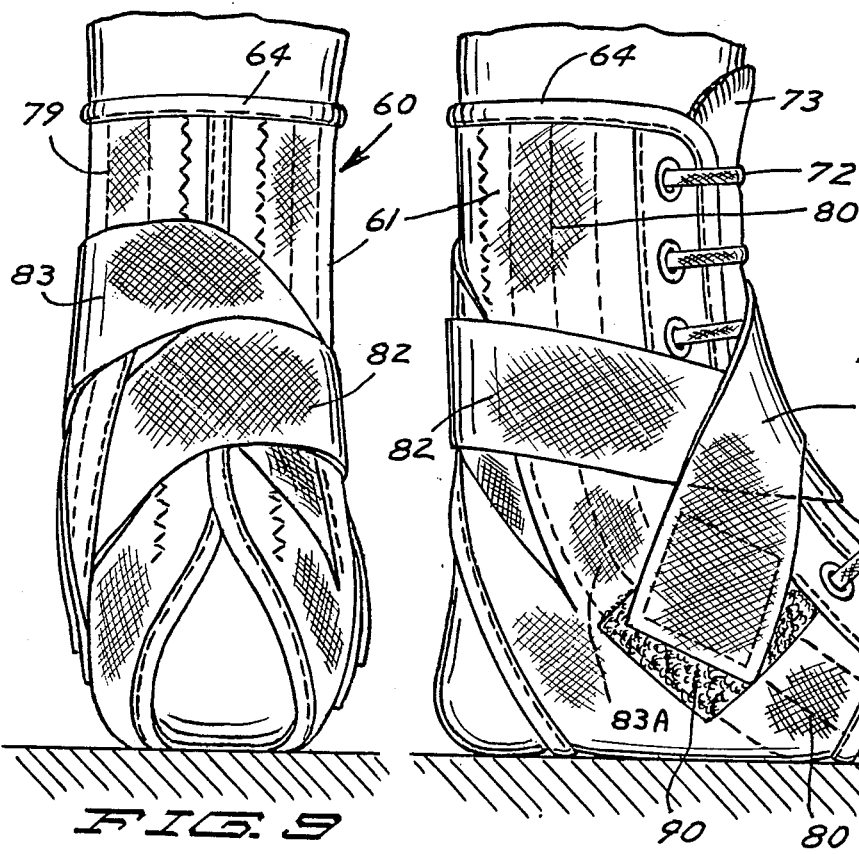

4,878,504

ANKLE BRACE WITH COMPRESSION STRAPS

BACKGROUND OF INVENTION

Foot and ankle injuries usually involve damage to ligaments either through hyperextension or extension beyond normal limitations, and through extension of the ligament in unintended direction as will occur upon abnormal movement of adjacent bones of the ankle and foot with respect to one another. The foot is composed of some 26 bones held together by small ligaments. Large tarsal bones make up the back half of the foot, while metatarsal bones connect the toes and comprise the front of the foot. The longitudinal arch of the foot runs from the heel through the end of the toes. The transverse arch of the foot runs across the tip of the metatarsal bones from the large to the small toe. The ankle joint is the complex articulation joint of the fibula and tibia with the ankle bone or talus and the tarsal bones. The outer ankle knob or lateral malleolus is at the lower end of the fibula. The inner ankle knob or medial malleolus is at the lower end of the tibia. These are held together by the tibial-fibular ligaments to form the top half of the ankle joint or the receptacle known as a mortice which is occupied by the talus. The talus is held by more ligaments. The ankle joint is meant to move only in one direction, flexture and extension or flexing and extending the foot up and down. Side to side movement of the foot and normal twisting motion occurs in the talo-calcaneal joint which lies just below the true ankle joint.

The ligament system holding the bones in proper relationship is particularly susceptable to injury during traumatic activity such as engaging in very active sports. For this reason, persons engaged in such activity usually wear protective gear such as an ankle wrap or an ankle brace. The object of such gear is to restrain the ankle and foot from abnormal rotational movement and from normal extension movement beyond undue limitation without unduly inhibiting normal foot movement so as to impede engagement in the particular acitivity.

SUMMARY OF INVENTION

The invention pertains to an ankle brace for generalized ankle support and for specifically placing the ankle joint and the talo-calcaneal joint in a state of compression prepatory to engaging in rigorous activity. The brace includes a jacket or base having a configuration to be wrapped around the foot and ankle in close conforming relationship. The base includes a first layer or liner and a second or outer layer substantially covering the liner on the lateral and medial sides of the foot and ankle. A plurality parallel spaced apart seams form a plurality of pockets that are vertical in the vicinity of the ankle and curve forwardly in the vicinity of the foot to generally follow the gradual curvature between the ankle and the foot. First and second elastic straps are secured to opposite sides of the base. The end of one strap is fixed to the lateral side of the base at the mid-foot region. The fixed end of the other is secured to the medial side of the base at the mid-foot region. The strap ends are secured between the inner and outer layers of the base in intersecting relationship to the seams that form the pockets in the base such that substantial portion of the end of the strap is fixed to the base. Tensioning of the strap is effective to distribute a tension force over a large portion of the base and accordingly the foot in a direction generally parallel to the traverse arch of the foot. Each strap has a portion that extends over the front superior portion of the foot to the opposite side of the base. The free ends of the straps are fastened in positin to maintain the strap portion over the top of the foot in tension and thereby compress the ankle and foot joints. Upon extension of the ankle and foot, the bones move from a compressed state to the normal state and then to an extended state against the inhibiting influence of the compression straps. The compression straps inhibit hyperextension of the ankle as well as abnormal twisting of the ankle.

IN THE DRAWINGS

FIG. 5 is a front elevational view of the ankle brace of FIG. 1 in an open configuration for purposes of illustration showing the inside thereof;

FIG. 6 is a rear elevational view of the ankle brace as shown in FIG. 5;

FIG. 7 is a side elevational view of an ankle brace according to a second form of the invention installed on a left foot and having the compression straps unfastened;

FIG. 8 is a side elevational view of the ankle brace and foot of FIG. 7 showing the opposite side thereof with the compression straps fastened;

FIG. 9 is a rear elevational view of the ankle brace and foot of FIG. 8; and

FIG. 10 is a enlarged sectional view of a portion of the ankle brace of FIG. 7 taken along the line 10—10 thereof.

DESBRIPTION OF PREFERRED EMBODIMENTS

Figure 1:
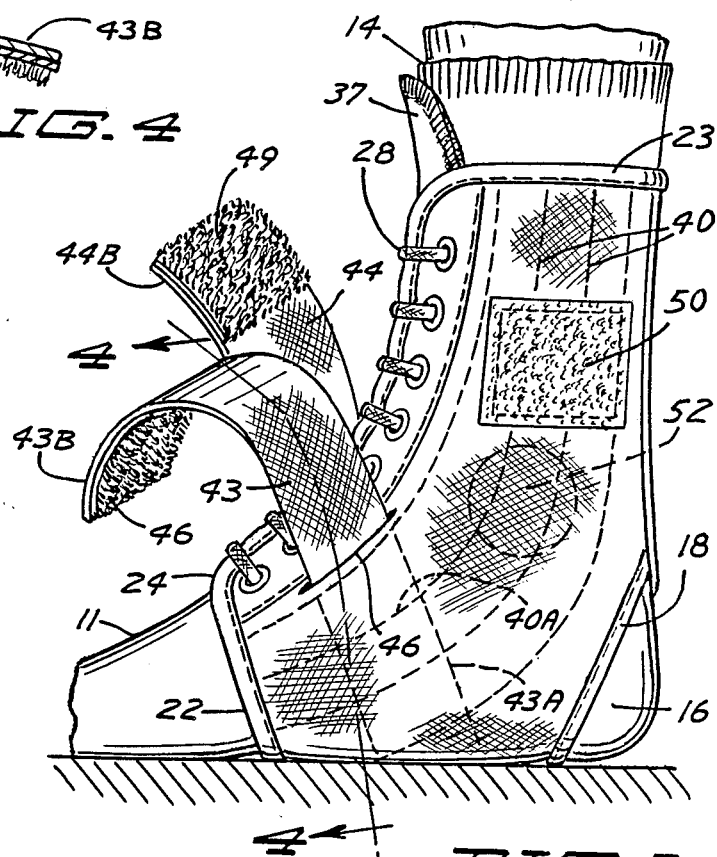
FIG. 1 is a side elevational view of an ankle brace according to a first form of the invention installed on a left foot and having the compression straps unfastened.
Figure 3:
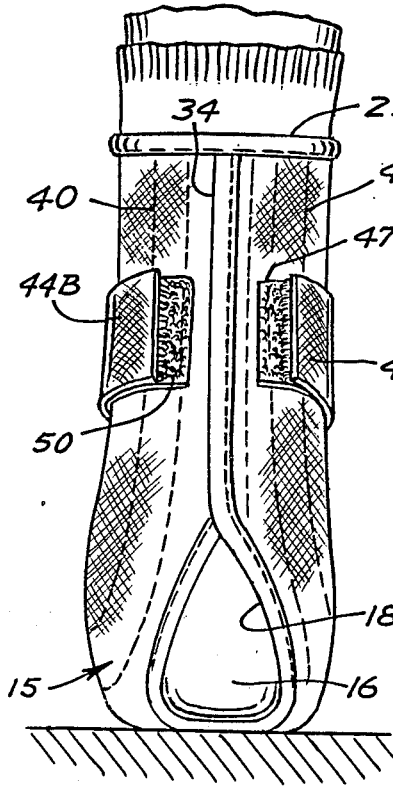
FIG. 3 is a rear elevational view of the ankle brace and foot of FIG. 2.
Figure 2:
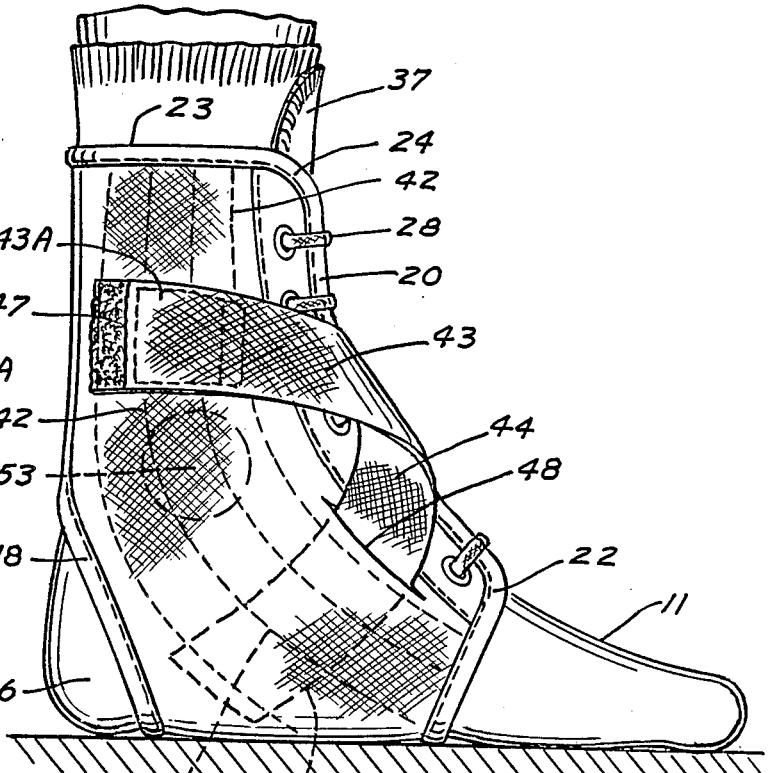
FIG. 2 is a side elevational view of the ankle brace and foot of FIG. 1 showing the opposite side thereof with the compression straps fastened.

Referring to the drawings, there is shown in FIGS. 1 through 3 an ankle brace according to one form of the invention indicated generally at 10 worn on a foot 11 and the associated ankle region 12 of a person wearing an optional stocking 14. The ankle joint is the joint between the leg and the foot in which the tibia and fibula above articulate with the talus below. The ankle is the region of the joint. The various bones comprising the ankle joint are interconnected by ligaments which are susceptable to damage upon hyperextension or movement of the bones apart from one another beyond normal limitation, and upon undue twisting or abnormal movement of the bones with respect to one another. The ankle brace 10 is effective to compress the bones in the ankle region toward one another in a relaxed state such that upon engagement in rigorous activity and extension of the ankle joint, the bones move through a normal position first and then to a normal extend position. The joint is inhibited from entering a hyperextended condition or from undue twisting movement.

As shown in FIG. 5, ankle brace 10 includes a flexible composite jacket or base 15 adapted to be wrapped in a conforming relationship around the foot and ankle. Base 15 has a top edge 23 that wraps aroung the lower leg forming a top opening to brace 10 when the base 15 is installed on a foot. A bottom edge 20 wraps around the midfoot to form a front opening. Forward edges 19, 20 come toward one another over the instep and front superior foot surface for fastening by suitable means. A continuous edge binding 24 is sewn to the various edges. Reinforcing strips 25 (FIGS. 1 and 2) are fixed to the forward edges 19, 20 and carry lace aperatures reinforced by eyelets 27. A common lace 28 is trained through the eyelets 27 to hold the forward edges 19, 20 in place relative to one another and bind the base 15 on the foot.

Base 15 includes an inner layer or liner 30 and an outer layer or cover 31 fixed to the inner layer 30 by the edge stitching associated with the binding 24. These layers are formed of a strong, flexible material such as canvas or vinyl that is relatively inelastic. A foam layer 32 can be interposed between the inner and outer layers 30, 31 for purposes of comfort of the wearer. Both inner and outer layers 30, 31 are formed of symmetrical half sections that are sewn together by a seam which becomes a rear vertical seam 34 and a short seam 35 that is horizontial when worn on the foot. The horizontal seam 35 and the vertical seam 34 are separated by heel opening 18.

A tongue 37 is fixed to the inside of base 15 proximate the lower end of one of the forward edges by a suitable stitching 38. The tongue 37 is adapted to cover the usual forward superior foot surface, ankle and lower leg portions between the front edges 19, 20 in conventional fashion.

Figure 4:
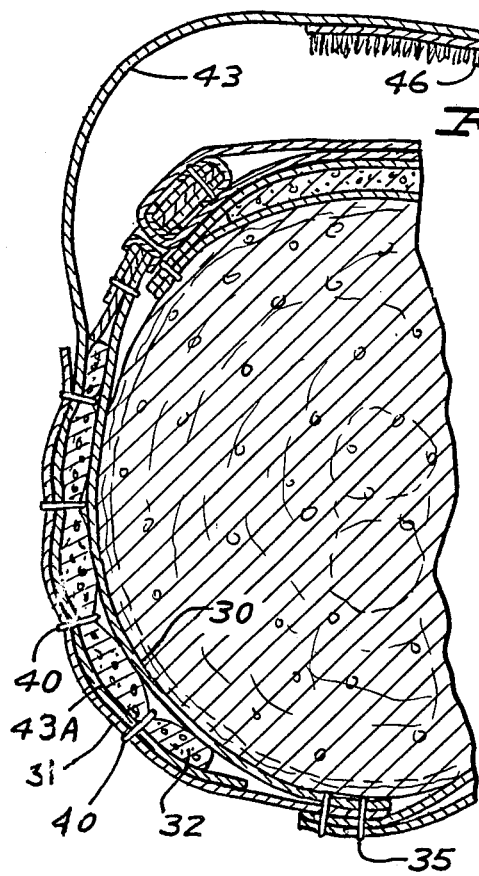
FIG. 4 is an enlarged sectional view of a portion of the ankle brace of FIG. 1 taken along the line 4—4 thereof.

As shown in FIG. 1, a plurality of lateral parallel, spaced-apart seams 40 are sewn on the lateral side of base 15. The seams 40 are substantially vertical near and extend downwardly from the upper edge 23 of base 15. Seams 40 are curved at an intermediate location in the vicinity of the ankle and extend forwardly toward lower edge 22. Seams 40 are curved to generally follow the transition between the lower leg, ankle and foot. As shown, there are four of the seams 40, although more or less can be provided. The seams 40 are sewn between the outer layer 31 and the intermediate foam layer 32 as shown in FIG. 4.

Referring to FIG. 2, a plurality of symmetrical medial seams 42 extend between the top edge 23 of base 15 and the lower edge 22 on the medial side thereof. The seams 42 intermediately curved between relatively vertical segments near the upper edge 23 and forwardly extending segments at the lower edge 22 in order to generally follow the curvature of the transition between the lower leg and the foot. Medial seams 42 are formed by stitching between the outer layer or cover 31 and the intermediate foam layer 32 of base 15.

Lateral and medial compression straps 43, 44 are fixed to the base 15 for extension about the front superior foot surface to opposite sides of the foot in order to place the unflexed foot and ankle in a state of compression. Each strap is comprised as an elongate flat member preferably longitudinally elastic. Lateral compression strap 43 has an end section 43A fixed to base 15 on the lateral side thereof at a location spanning an area positioned beneath and forward of the lateral malleolus indicated at 52 in FIG. 1. End section 43A is imbedded between the outer layer 31 and the inner layer 30, extending through an opening or slit 46 formed in the outer layer 31 rearward of the lateral forward edge 19. End section 43A is of sufficient length to intersect and span segments of the lateral seams 40. End section 43A is fixed to base 15 by segments 40A of the lateral seams 40. Lateral seams 40 are sewn through the end section 43A of compression strap 43 at lines of intersection. The seam segments 40A extend through the outer layer 31, end section 43A and the intermediate foam layer 32. Tension applied to the compression strap 43 is distributed about the lateral side of base 15 by virtue of the plurality of seam segments 40A fixing the end section 43A. Compression pressure as a result of the tensioning force is distributed ganerally across the mid-lateral foot region.

The free end 43B of lateral compression strap 43 is equipped with a fasting means or inwardly facing pad 46. The end section 43A is fastened to the side of base 15 in an orientation such that the free end 43B is directed to extend upwardly and forwardly to with respect to the foot 11 as shown in FIG. 1 so as to enable it to be wrapped upwardly over the front superior foot portion. A stationary second lateral compression strap fastening means or pad 47 is secured to the base 15 on the medial side at a location above the medial malleolus. Pad 47 is outwardly facing in position to engage the fastening pad 46 on the free end 43B of compression strap 43. The fastening pads 46, 47 can be comprised of synthetic material of the type that adheres when pressed together such as that sold under the trademark Velcro. Compression strap 43 has a length such that the strap will be in tension when fastening pads 46 and 47 are connected. The tension force is distributed about the laterial side of the foot tending to bind the bones and ligaments on that side of the foot toward the upper mortice of the ankle joint formed by the tibia and fibula. The width of the lateral compression strap fastening pads 46, 47 permits a measure of adjustability of the tension in compression strap 43 and allows for different sizes of feet as well.

A medial compression strap 44 is symmetrical to the lateral compression strap 43 and is also formed of a rectangular length of longitudinally elastic material. An end section 44A is fixed to the medial side of base 15 and spans an area along the side of base 15 is intersecting relationship to the several medial seams 42 at a location beneath the medial malleolus. End section 44A is embedded between the inner and outer layers of vase 15 and is fastened between the outer layer 31 and intermediate layer 32 by segments of the medial seams 42. It extends in an upwad and forward direction through a slit 48 provided in outer layer 31. Medial seam segments 42A (FIG. 2) intersect th longitudinal axis of the end section 44A of strap 44 to securely fasten it to an enlarged area of the medial side of base 15. As shown, four medial seam segments 42B are sewn to the strap end 44A whereby a tenson force applied to the strap 44 will be distributed over the medial side of the foot 11.

The free end 44B of medial compression strap 44 is equipped with a first fastening means or pad 49 that is inwardly facing when the strap 44 is wrapped around the foot. A stationary fastening means or pad 50 is secured to base 15 on the lateral side thereof at a location above the lateral malleolus and is outwardly facing to engage the fastening pad 49 on the free end 44B of the medial compressing strap 44. Compression strap 44 has a length such that the strap will be in tension when fastening pad 49 is secured to the outwardly facing fastening pad 50. The tension force is distributed above the medial side of the foot tending to bind the bones and ligaments on that side of the foot toward the ankle joint.

In use, base 15 can be contoured for wearing specifically on the left or right foot, or it can be universally cut to be worn on either foot. As shown in FIGS. 1 though 3, base 15 is installed on a left foot and lace 28 is drawn tight. Base 15 alone gives a measure of support to the ankle region. Each of the compression straps is then put in place by stretching across the front superior foot portion to the opposite side of the base and fastening it on the stationary fastening pad above the malleolus. The compression straps are preferably elastic with a high spring constant so as to resiliantly bind the lower foot portion to the lower leg portion at the ankle joint and place the ankle joint in a slight state of compression prepatory to engagement in rigorous activity.

A foot wearing brace 10 commences activity in a slightly compressed condition and moves from there through the normal state into an extended state upon rigorous activity. The foot does not reach the hyperextended state thus avoiding injury to the ligaments. Brace 10 also prevents the foot from undue twisting about abnormal axes.

A second form of ankle brace according to the invention shown in FIGS. 7 through 10 is indicated generally at 60 have a base 61 configured closely conform to the lower leg, ankle 62 and foot 63, top edge 64 that wraps around the lower leg, and a lower edge 65 that wraps around the mid foot portion. First and second forward edges 67, 68 come toward one another around the front of the foot, lower leg and ankle and carry lace eyelets 71 that are engaged by a common lace 72 to tightly hold the base 61 in place. A binding 69 is secured to the various edges. A tongue 73 wraps aroung the front lower leg, foot and ankle in covering relationship to them in spanning the area between the front edges 67, 68.

Base 60 is configured similar to a base 15 shown in FIG. 1 through 3, and has an outer layer 75, and inner layer 76 and intermediate foam layer 77 as shown in the segmented portion of FIG. 10. The inner and outer layers 76, 75 are preferably of a flexible sheet like material such as canvas or vinyl. The intermediate foam layer 77 is for the comfort of the wearer. A plurality of lateral seams 79 extend from the upper edge 64 downwardly to the lower edge 65 of the base 61. The lateral seams 79 follow the transition between the lower leg, ankle and foot. The seams are relatively vertical in the vicinity of the upper edge 64, curve forward in the vicinity of the ankle 62 and extend forwardly and slightly downward in the vicinity of the forward edge 65 of base 61. As shown in FIG. 10, the seams 79 are formed by stitches that are sewn through the side wall of the base 61 including the outer layer 75, foam layer 77 and inner layer 76.

In symmetrical relationship, a plurality of parallel spaced apart medial seams 80 extend from the top edge 64 of on the medial side thereof downwardly and curve forward in the region of the ankle 12 extending to the bottom edge 65 of base 61. The lateral and medial seams generally follow the contour of the transition between the lower leg to the foot and lend a measure of stability to the base 61 in the direction of normal flexure of the foot.

Brace 60 has lateral and medial compression straps 82, 83 each fixed at one end to base 61 for wrapping aroung base 61 in tension to place the foot and ankle in a state of compression prepatory to commencement of rigorous activity. The compression straps are anchored to the base 61 by segments of the lateral and medial seams 79, 80 which serve also to distribute the tension force applied by the compression straps about a large portion of the side of the foot. As shown in FIG. 7, the lateral compression strap 82 has an end section 82A fixed to the base 61 on the lateral side thereof. Strap 82 is a flat rectangular member that is relatively wide, i.e. two inches, and longitudinally elastic enabling it to be wrapped around the foot in tension. End section 82A is embedded beteen the outer layer 75 and inner layer 76 of base 61. The end section 82A intersects the lateral seams 79 and is securely held in place by them. As shown in FIG. 10, the lateral seams 79 pass through the outer layer 75, the end section 82A, the intermediate foam layer 77 and the inner layer 76. End section 82A is orientated to direct compression strap 82 to extend rearwardly and upwardly from the end section 82A through a slit 84 provided in the outer layer 75.

The free end 82B of lateral compression strap 82 carries a first fastening pad 85. A second fastening pad 86 is secured to the base 61 on the lateral side thereof at a location beneath and forward of the lateral malleolus in the vicinity of the fixation points of the end section 82A of strap 82. The first and second fastening pads 85, 86 each carry synthetic material of the type that adheres when pressed together. When fastened, lateral compression strap 82 is stretched across the back of the foot above the heel, above or over the medial malleolus, over the front superior foot portion and then fastened to the second fastening pad 86.

Medial compression strap 83 is symmetrically fastened to the base 61 with an end section 83A embedded between the inner and outer layers 75, 76 of base 61. The free end 83A of medial compression strap 83 carries a first medial compression strap fastening pad 89. A second fastening pad 90 is fastened to the base 61 on the medial side in covering relationship to a mid-portion of the foot beneath medial malleolus. The medial compression strap is fastened in symmetrical relationship to the lateral compression strap. The medial compression strap is extended around the back of the foot above the heel to the lateral side of base 61. It extends over or slightly above the lateral malleolus then to the second medial comression strap fastening pad 90 as shown in FIG. 8.

In use, the foot is placed in the base 61 with the toes extending through the front opening and the heel extending through the back opening. The lace 72 is tightened with the foot in a relaxed position, and the compression straps 82, 83 are secured as shown in FIGS. 8 and 9. The compression straps place the foot and ankle in the state of compression prepatory to engaging in rugged activity.

While there have been shown and described certain preferred embodiments of the invention, it will apparent that deviations can be made without departing from the scope and spirit of the invention.

The embodiments of the invention in which an exclusive property or privilege is claimed are defined as follows:

1. An ankle brace to be worn on a foot and ankle in encompassing relationship to the lateral malleolus and medial melleolus of the ankle on the lateral and medial sides of the foot respectively, comprising:
   a base of flexible sheet-like material shaped to encompass the ankle region and proximate lateral and medial portions of the foot; said base having medial and laterial forward edges that come together toward one another over the forward ankle and from superior foot portion when the base is installed on the foot, and means for fastening the medial and lateral forward edges with respect to one another to secure the base with respect to an ankle and foot;

said base including an outer layer and an inner layer of sheet-like material;

said base having a plurality of medial seams sewn between the outer and inner layers located on the medial side thereof in parallel spaced apart relationship and being forwardly curved extending from the region of the ankle to the mid-foot region;

said base having a plurality of lateral seams sewn between the outer and inner layers located on the lateral side thereof in parallel spaced apart relationship and being forwardly curved extending from the region of the ankle to the mid-foot region;

a medial compression strap comprised as a flat elongate longitudinal member having a fixed end section fixed to the medial side of the base and a free end extendable around the base, said fixed end section having a width and length of sufficient dimension to span segments of said plurality of medial seams, said end section being fixed to the base by said segments of said plurality of medial seams and being embedded between the inner and outer layers of the base;

a first medial comprssion strap fastening means located on the free end of the medial compression strap, and second medial compression strap fastening means located on the lateral side of the base above the area covering the lateral malleous and positioned to be releasably engaged by the first fastening means upon wrapping the medial compression strap in tension around the front superior foot surface portion of the base and the vicinity of the lateral malleolus, said fixed end section of the medial compression strap fixed to the base orientated so that the medial compression strap is directed to extend forwardly and upwardly so that it can extend from the fixed end section across the front superior foot surface to the second medial compression strap fastening means;

a lateral compression strap comprised as a flat elongate longitudinal member having a fixed end section fixed to the base and a free end extendable around the base, said fixed end section having a width and a length of sufficient dimension to span segments of said plurality of lateral seams, said end section being fixed to the base by said segments of said plurality of lateral seams and being embedded between said inner and outer layers of the base; and a first lateral compression strap fastening means located on the free end of the lateral compression strap, and second lateral compression strap fastening means located on the medial side of the base above the area covering the medial malleous and positioned to be releasable engaged by the first fastening means upon wrapping the lateral compression strap in tension around the front superior foot portion of the base and the vicinity of the medial malleolus, said fixed end section of the lateral compression strap fixed to the base orientated so that the lateral compression strap is directed to extend forwardly and upwardly so that it can extend from the fixed end section across the front superior foot surface to the second lateral compression strap fastening means, said base having an opening for extension of the free end of the lateral compression strap from between said outer and inner layers in said forward and upward direction.

2. The ankle brace of claim 1 wherein: said medial and lateral forward edges have lace openings, said for fastening the forward edges with respect to one another comprising a lace, and including a tongue attached proximate one of said forward edges and movable into covering relationship to the ankle and superior portion of the foot.

3. The ankle brace of claim 1 wherein: said first and second fastening means of the lateral and medial compression strap are comprised of pads of synthetic material of the type that adheres when pressed together.

4. The ankle brace of claim 1 wherein:·said lateral and medial compression straps are longitudinally elastic.

5. The ankle brace of claim 4 wherein: said first and second fastening means of the lateral and medil compression straps are comprised of pads of synthetic material of the type that adheres when pressed together.

6. An ankle brace to be worn on a foot and ankle in encompassing relationship to the lateral malleolus and medial malleolus of the ankle on the lateral and medial sides of the foot respectively, comprising:

a base of flexible sheet-like material shaped to encompass the ankle region and proximate lateral and medial portions of the foot;

said base having medial and lateral forward edges that come together toward one another over the forward ankle and front superior foot pertion when the base is installedd on a foot, and means for fastening the medial and lateral forward edges with respect to one another to secure the base with respect to an ankle and foot;

said base including an outer layer and an inner layer of sheet-like material;

said base having a plurality of medial seams sewn between the outer and inner layers located on the medial side thereof in parallel spaced apart relationship and being forwardly curved extending from the region of the ankle to the mid-foot region;

said base having a plurality of lateral seams sewn between the outer an inner layers located on the lateral side thereof in parallel spaced apart relationship and being forwardly curved extending from the region of the ankle to the mid-foot region;

a medial compression strap comprised as a flat elongate longitudinal member having a fixed end section fixed to the medial side of the base and a free end extendable aroung the base, said fixed end section having a width and length of sufficient dimension to span segments of said plurality of medial seams, said end section being fixed to the base by said segments of said plurality of medial seams and being embedded between the inner and outer layers of the base;

a first medial compression strap fastening means located on the free end of the medial compression strap, and a second medial compression strap fastening means located on the medial side of the base beneath the area covering the medial malleolus, said end section of the medial compression strap fixed to the base orientated so that the medial compression strap is directed to extend rearwardly and upwardly so that it cam extend from the fixed end section and be wrapped behind the foot above the heel, aroung the lateral malleolus, over the front superior foot portion to the second medial compression strap fastening means;

a lateral compression strap comprised as a flat elongate longitudinal member having a fixed end section fixed to the lateral side of the base and a free end extendable around the base, said fixed end section having a width and a length of sufficient dimension to span segments of said plurality of lateral seams, said end section being fixed to the base by said segments of sai plurality of lateral seams and being embedded between said inner and outer layers of the base;

a first latera compression strap fastening means located on the free end of the lateral compression strap, and a second lateral compression strap fastening means being located on the lateral side of the base beneath the area covering the lateral malleolus, said end section of the lateral compression strap fixed to the base orientated so that the lateral compression strap is directed to extend rearwardly and upwardly so that it can extend from the fixed end section and be wrapped behind the foot above the heel, around the medial melleolus, over the front superior foot portion to the second lateral compression strap fastening means;

said base having slit like openings for extension of the free ends of the medial and lateral compression straps from between said outer and inner layers of the base in said rearwardly and upwardly directions.

7. The ankle brace of claim 6 wherein: said medial and lateral compression straps are formed of longitudinally elastic material.

8. The ankle brace of claim 7 wherein: said first and second fastening means of the lateral and medial compression straps are comprised of pads of synthetic material of the type that adheres when pressed together.

9. An ankle brace to be worn on a foot and ankle in encompassing relationship to the lateral malleolus and medial malleolus of the ankle on the lateral and medial sides of the foot respectively, comprising:

a base of flexible sheet-like material shaped to closely conform to the foot and ankle region in covering relationship to the medial and lateral malleolus, said base having an upper edge in surrounding relation to the lower leg above the ankle, and a bottom edge in surrounding relation to the midfoot, an elongate, longitudinally elastic, flat medial compression strap having one end section fixed to the base and an opposite free end;

means fixed the one end section of the medial compression strap to the medial side of the base including first, second and third parallel spaced apart medial seams orientated transversely to the longitudinal dimension of the medial compression strap extending from the vicinty of the upper edge of the base on the medial side to the vicintiy of the bottom edge of the base being intermediately curved between relatively vertical segments near the upper edge of the base and forwardly extending segments near the bottom edge in order to generally follow the curvature of the transition between the lower leg and the foot, each seam intersecting and extending substantially across the width of the end section of the medial compression strap thereby fixing the medial compression strap to the medial side of the base whereby a tension force exerted on the compression strap is distributed over the medial side of the base, sid medial seams orientating the end section of the medial compression strap so that it is directed to extend forwardly and upwardly when the base is fitted on a foot for extendsion of the free end of the medial compression strap from the fixed end across the front superior portion of the foot surface to the lateral side of the base;

a first medial compression strap fastener located on the free end of the medial compression strap, and a second medial compression strap fastener and located on the lateral side of the base above the area covering the lateral malleolus so that the medial compression strap can be extended in tension from the fixed end section across the front superior foot surface to the second medial compression strap fastener;

an elongate, longitudinally elastic, flat lateral compression strap having one end section fixed to the base and an opposite free end;

means fixing the one end section of the lateral compression strap to the lateral side of the base including first, second and third parrallel spaced apart lateral seams orientated transversely to the longitudinal dimension of the lateral compression strap extending from the vicintiy of the upper edge of the base on the lateral sid to the vicintiy of the bottom edge of the base being intermediately curved between relatively vertical segments near the upper edge of the base and forwardly extending segments near the bottom edge in order to generally follow the curvature of the transition between the lower leg and the foot, each seam intersection and extending substantially across the width of the end section of the lateral compression strap thereby fixing the lateral compression strap to the lateral side of the base whereby a tension force exerted on the lateral compresson strap is distributed over the lateral side of the base, said lateral seams orientating the end section of the lateral compression strap so that the lateral compression strap is directed to extend forwardly and upwardly when the base is fitted on a foot for extension of the free end of the lateral compression strap over the front superior foot surface of the medial side of the base;

a first lateral compression strap fastener located on the free end of the lateral compression strap, and a second lateral compression strap fastener connectable with the first lateral compression strap fastener and located on the medial side of the base above the area covering the medial malleolus so that the first lateral compression strap fastener can be connected to the second lateral strap fastener with the lateral compression strap extended from the fixed end of the base in tension across the front superior foot surface.

10. The ankle brace of claim 9 wherein: said base is a composite of an inner layer of flexible sheet-like material and an outer layer of flexible sheet-like material, said end sections of the medial and lateral compression straps being embedded between the inner and outer layers of the base, said medial and lateral seams being formed between the inner and outer layers of the base;

said base having a front opening defined by front edges that close toward one another across portions of the front superior foot, ankle and lower leg, and including lace means for securing the first and second forward edges of the base with respect to one another when the base is fitted on a foot.

11. The ankle brace of claim 10 wherein:
said base includes an upper edge that wraps around the ankle, and a lower edge that wraps around the mid-foot portion, said lateral seams extending on the lateral side of the base from the upper edge of the base to the lower edge and being intermediately curved in the area of transition between the ankle and the foot;
said medial seams extending from the upper edge of the base to the lower edge of the base on the medial side of the base and being intermediately curved in the vicinity of the transition between the ankle and the foot.

12. The ankle brace of claim 11 including: an intermediate layer of foam disposed between the inner and outer layers.

13. The ankle brace of claim 11 wherein: said first and second fasteners of the medial and lateral compression straps are comprised of pads of synthetic material of the type that adheres when pressed together.

14. An ankle brace to be worn on a foot and ankle in encompassing relationship to the lateral malleolus and medial malliolus of the ankle on the lateral and medial sider of the foot respectively, comprising:
a base of sheet-like material shaped to closely conform to the foot and ankle region in covering relationship to the medial and lateral malleolus said base having an upper edge in surrounding relation to the lower leg above the ankle, and a bottom edge in surrounding relation to the mid-foot;
an elongate, longitudinally elastic, flat medial compression strap having one end section fixed to the base and an opposite free end;
means fixing the one end section of the medial compression strap to the medial side of the base including first, second and third parallel spaced apart medial seams orientated transversely tothe longitudinal dimension of the medial compression strap extending from the vicintiy of the upper edge of the base on the medial side to the vicintiy of the bottom edge of the base being intermediately curved between relatively vertical segments near the upper edge of the base and forwardly extending segments near the bottom edge in order to generally follow the curvature of the transition between the lower leg and the foot, each seam intersecting and extending substatially across the width of the end section of the medial compression strap thereby fixing the media compression strap to the medial side of the base whereby a tension force exerted on the compression strap is distributed over the medial side of the base, said medial seams orientating the end section of the medial compression strap so that the medial compression strap is directed to extend rearwardly and rewardly when the base is fitted on a foot for extension of the free end of the medial compression strap from the fixed and section to be wrapped behind the foot above the heel, around the lateral malleolus, over the front superior foot portion to the medial side of the brace
a first medial compression strap fastener located on the free end of the medial compression strap, and a second medial compression strap fastener connectable with the first medial compression strap fastener and located on the medial side of the base beneath the covering the medial malleolus so that the medial compression strap can be extended in tension from the fixed end section behind the foot and above the heel, around the lateral malleolus, over the front superior foot portion to the second medial compression strap fastener for commection with the second medial compression strap fastener;
an elongate longitudinally elastic, flat lateral compression strap having one end section fixed to the base and an opposite free end;
means fixing the one end section of the lateral compression strap to the lateral side of the base including first, second and third parallel spaced apart lateral seams orientated transversely to the longidutinl dimension of the lateral compression strap extending from the vicintiy of the upper edge of the base on the lateral side to the vicintiy of the bottom edge of the base being intermediately curved between relatively vertical segments near the upper edge of the base and forwardly extending segments near the bottom edge in order to generally follow the curvature of the transition between the lower leg and the foot, each seam intersecting and extending substantially across the width of the end section of the lateral compression strap thereby fixing the lateral compression strap to the lateral side of the base whereby a tension force exerted on the lateral compression strap is distributed over the lateral side of the base, said lateral seams orientating the end section of the lateral compression strap so that the lateral compression strap is directed to extend rearwardly and upwardly when the base is fitted on a foot for extension of the free end of the lateral compression strap from the fixed end behind the foot above the heel, around the medial malleolus, over the front superior foot portion to the lateral side of the base;
a first lateral compression strap fastener located on the free end of the lateral compression strap, and a second lateral compression strap fastener connectable with the first lateral compression strap fastener and located on the lateral side of the base beneath the area covering the lateral malleolus so that the lateral compression strap can be extended in tension from the fixed end section behind the foot above the heel, around the medial malleolus, over the front superior foot portion to th second lateral compression strap fastener for connection with the second lateral compression strap fastener.

15. Ankle of brace of claim 14 wherein: said base is a composite of an inner layer of flexible sheet-like material and an outer layer of flexible sheet-like material, said end sections of the medial and lateral compression straps being embedded between the inner and outer layers of the base, said medial and lateral seams being formed between the inner and outer laters of the base;
said base having a front opening defined by front edges that close toward one another across portions of the front superior foot, ankle and lower leg, and including lace means for securing the first and second forward edges of the base with respect to one another when the base is fitted on a foot.

16. The ankle brace of claim 15 including: an intermediate layer of foam disposed between the inner and outer layers.

17. The ankle brace of claim 15 wherein: said first and second fasteners of the medial and lateral compression straps are comprised of pads of synthetic materal of the type that adheres when pressed together.

* * * * *

UNITED STATES PATENT AND TRADEMARK OFFICE
CERTIFICATE OF CORRECTION

PATENT NO.  : 4,878,504

DATED       : November 7, 1989

INVENTOR(S) : RONALD E. NELSON

It is certified that error appears in the above-identified patent and that said Letters Patent is hereby corrected as shown below:

| | |
|---|---|
| Col 1, l 53 | following "plurality" insert --of-- |
| Col 1, l 64 | following "that" insert --a-- |
| Col 2, l 4 | "positin" should be --position-- |
| Col 2, l 40 | "a" first occurance should be --an-- |
| Col 2, l 43 | "DESBRIPTION" should be --DESCRIPTION-- |
| Col 3, l 1 | "aroung" should be --around-- |
| Col 4, l 11 | "ganerally" should be --generally-- |
| Col 4, l 45 | "vase" should be --base-- |
| Col 5, l 24 | "have" should be --having-- |
| Col 5, l 32 | "aroung" should be --around-- |
| Col 5, l 65 | "aroung" should be --around-- |
| Col 6, l 33 | "83A" should be --83B-- |
| Col 7, l 1 | "from" should be --front-- |
| Col 8, l 5 | following "said" insert --means-- |
| Col 8, l 18 | "medil" should be --medial-- |
| Col 8, l 30 | "pertion" should be --portion-- |
| Col 8, l 31 | "installedd" should be --installed-- |
| Col 8, l 44 | "an" should be --and-- |
| Col 8, l 51 | "aroung" should be --around-- |
| Col 8, l 66 | "cam" should be --can-- |
| Col 8, l 68 | "aroung" should be --around-- |
| Col 9, l 10 | "sai" should be --said-- |

UNITED STATES PATENT AND TRADEMARK OFFICE
CERTIFICATE OF CORRECTION

PATENT NO. : 4,878,504

DATED : November 7, 1989

INVENTOR(S) : RONALD E. NELSON

It is certified that error appears in the above-identified patent and that said Letters Patent is hereby corrected as shown below:

| | |
|---|---|
| Col 9, l 13 | "latera" should be --lateral-- |
| Col 9, l 23 | "melleolus" should be --malleolus-- |
| Col 9, l 52 | "fixed" should be --fixing-- |
| Col 10, l 2 | "sid" should be --said-- |
| Col 10, l 5 | "extendsion" should be --extension-- |
| Col 10, l 11 | following "fastener" insert --connectable with the first medial compression strap fastener-- |
| Col 10, l 16 | following "strap" insert --for connection with the second medial compression strap-- |
| Col 10, l 23 | "parrallel" should be --parallel-- |
| Col 10, l 27 | "sid" should be --side-- |
| Col 10, l 33 | "intersection" should be --intersecting-- |
| Col 11, l 24 | "malliolus" should be --malleolus-- |
| Col 11, l 25 | "sider" should be --sides-- |
| Col 11, l 38 | "tothe" should be --to the-- |
| Col 11, l 50 | "media" should be --medial-- |
| Col 11, l 56 | "rearwardly and rearwardly" should be --rearwardly and upwardly-- |
| Col 11, l 59 | "and" should be --end-- |
| Col 12, l 5 | "commection" should be --connection-- |
| Col 12, l 54 | "laters" should be --layers-- |

UNITED STATES PATENT AND TRADEMARK OFFICE
CERTIFICATE OF CORRECTION

PATENT NO. : 4,878,504

DATED : November 7, 1989

INVENTOR(S) : RONALD E. NELSON

It is certified that error appears in the above-identified patent and that said Letters Patent is hereby corrected as shown below:

Col 12, l 66      "materal" should be --material--

Signed and Sealed this

Eleventh Day of December, 1990

*Attest:*

HARRY F. MANBECK, JR.

*Attesting Officer*     *Commissioner of Patents and Trademarks*